(12) United States Patent
Ying et al.

(10) Patent No.: US 12,013,386 B1
(45) Date of Patent: Jun. 18, 2024

(54) SAMPLE PROCESSING AND ANALYZING DEVICE FOR SOIL ANALYSIS IN KARST AREA

(71) Applicant: Nanjing Institute of Environmental Sciences, MEE, Nanjing (CN)

(72) Inventors: Rongrong Ying, Nanjing (CN); Wenbing Ji, Nanjing (CN); Lingya Kong, Nanjing (CN); Yuanyuan Lu, Nanjing (CN); Caiyi Zhao, Nanjing (CN); Zhewei Hu, Nanjing (CN); Yanhong Feng, Nanjing (CN); Xiaoyu Zhang, Nanjing (CN); Aijing Yin, Nanjing (CN); Qi Li, Nanjing (CN)

(73) Assignee: Nanjing Institute of Environmental Sciences, MEE, Nanjing (CN)

( * ) Notice: Subject to any disclaimer, the term of this patent is extended or adjusted under 35 U.S.C. 154(b) by 0 days.

(21) Appl. No.: 18/329,691

(22) Filed: Jun. 6, 2023

(30) Foreign Application Priority Data

Oct. 27, 2022 (CN) .......................... 202211328128.1

(51) Int. Cl.
*G01N 1/00* (2006.01)
*G01N 1/28* (2006.01)
(Continued)

(52) U.S. Cl.
CPC ............. *G01N 33/24* (2013.01); *G01N 1/286* (2013.01); *G01N 1/34* (2013.01); *G01N 2001/2866* (2013.01)

(58) Field of Classification Search
None
See application file for complete search history.

(56) References Cited

U.S. PATENT DOCUMENTS 9,132,407 B1 * 9/2015 Medoff .................... D21B 1/10

FOREIGN PATENT DOCUMENTS

| CN | 205887006 U | 1/2017 |
| CN | 109248741 A | 1/2019 |

(Continued)

OTHER PUBLICATIONS

Notice of Grant, issued in CN202211328128.1 (priority application), by CNIPA, dated Apr. 22, 2023.
(Continued)

*Primary Examiner* — Jyoti Nagpaul
(74) *Attorney, Agent, or Firm* — Zhu Lehnhoff LLP

(57) ABSTRACT

A sample processing and analyzing device for soil analysis in a karst area comprises a mounting unit, a processing unit arranged on the mounting unit, and an analyzing unit arranged on the mounting unit and connected with the processing unit through a feeding unit. The design of the damping component can control the grinding force to avoid sample crushing. The installation disc can be effectively clamped by the second axial moving component to move the sample position according to the grinding requirements, facilitating step-by-step polishing. The feeding unit sends the sample to the analysis unit through a conveyor belt for effective analysis. The sample processing and analyzing device can effectively process a soil concretion sample into a sample for analysis, has the advantages of easy operation, high degree of automation and high efficiency, and is suitable for mass popularization.

9 Claims, 3 Drawing Sheets

(51) Int. Cl.
*G01N 1/34* (2006.01)
*G01N 33/24* (2006.01)

(56) References Cited

FOREIGN PATENT DOCUMENTS

| | | |
|---|---|---|
| CN | 209124071 U | 7/2019 |
| CN | 213727031 U | 7/2021 |
| CN | 216847108 U | 6/2022 |
| CN | 217568987 U | 10/2022 |
| WO | 2020199290 A1 | 10/2020 |
| WO | 2021228754 A2 | 11/2021 |

OTHER PUBLICATIONS

Zhanqiao Patent Search Report, issued by Zhanqiao Patent Agency, dated Oct. 27, 2022.

* cited by examiner

SAMPLE PROCESSING AND ANALYZING DEVICE FOR SOIL ANALYSIS IN KARST AREA

REFERENCE TO RELATED APPLICATIONS

The present application claims the priority of Chinese patent application No. 202211328128.1, filed on 2022 Oct. 27, the entire disclose of which is incorporated herein by reference.

TECHNICAL FIELD OF THE INVENTION

The present disclosure relates to the technical field of soil analysis and detection, in particular to a sample processing and analyzing device for soil analysis in a karst area.

BACKGROUND OF THE INVENTION

China is one of the countries with the largest concentrated and continuous distribution area of karst areas in the world. The total area of karst areas is $344.3 \times 10^4$ km$^2$, accounting for about one third of land area. In recent years, it has been reported that the soil heavy metals in karst areas in southwest China seriously exceed the standard, which is closely related to geologic origin. At the same time, researches of related scholars show that the content of soil heavy metals in karst areas where iron-manganese concretion is developed is higher than that in non-karst areas.

Iron-manganese concretion is an important carrier of soil heavy metals in karst areas. The causes of iron-manganese concretion in soil with high geological background are explored, which can provide a basis for ecological risk management and land safety utilization of soil heavy metals in high geological background areas. By means of microscopes, chemical analysis and other means, the characteristics of iron-manganese concretion are researched from the aspects of morphology, element geochemistry, mineralogy and adsorption and desorption performance, so that the indicative significance of iron-manganese concretion characteristics to soil occurrence is revealed.

However, the thickness of a concretion sample collected directly from the soil is thick, which is not conducive to microscopic observation. Therefore, the collected sample needs to be processed for microscopic observation. At present, processing and analysis of the sample by workers in the same field are carried out separately and are complex. The present disclosure provides an analyzing device with sample processing and analyzing functions, which is more convenient and labor-saving.

SUMMARY OF THE INVENTION

Aiming at the problem of complicated flow in the prior art, the present disclosure provides a sample processing and analyzing device for soil analysis in a karst area.

Through the technical scheme of the present disclosure, a sample processing and analyzing device for soil analysis in a karst area includes a mounting unit, a processing unit arranged on the mounting unit, and an analyzing unit arranged on the mounting unit and connected with the processing unit through a feeding unit.

The mounting unit includes a first mounting table and a second mounting table connected with the first mounting table.

The processing unit comprises a pretreatment component arranged on the second mounting table and a grinding unit connected with the pretreatment component through the feeding unit.

The grinding unit comprises a first fixed component, a second fixed component and a grinding component.

The first fixed component comprises a first axial component and a second axial moving component respectively arranged on the first mounting table.

The second fixed component comprises a radial moving component and a damping component arranged on the radial moving component; the radial moving component comprises a radial mounting guide rail and a moving base arranged on the radial mounting guide rail; the damping component comprises a mounting base and a spring component for connecting the mounting base with the moving base.

The grinding component comprises a feeding device arranged on the second mounting table, a grinding disc arranged at the bottom of the mounting base, a mounting disc arranged on the second axial moving component and located under the grinding disc, and a driving component arranged inside the mounting base and used for supplying power for the grinding disc.

The grinding disc comprises a mounting substrate arranged at the bottom of the mounting base, and a first grinding piece and a second grinding piece axially arranged on the mounting substrate from inside to outside.

A closing plate for controlling a port switch at a lower end of the sample placing groove is arranged on the first axial component:

The pretreatment component comprises a treatment cavity arranged on the second mounting table, a cleaning module arranged in the treatment cavity and used for cleaning the sample, and an air-drying module arranged on the treatment cavity and used for air-drying the cleaned sample.

The feeding device comprises a first abrasive storage cavity for storing coarse polishing materials, a second abrasive storage cavity for storing fine polishing materials, and a feeding tube mounted on the first mounting table through an electric rotating shaft and used for feeding polishing materials to the sample placed in the sample placing groove: a feeding end of the feeding tube can be respectively connected with the first abrasive storage cavity and the second abrasive storage cavity.

And the analyzing unit comprises a microscope module for microscopic observation of the collected sample, and a photographing module for photographing and recording observed typical phenomena.

Further, the microscope module includes either one or two of an optical microscope and a field emission scanning electron microscope.

That is to say, through the optical microscope and field emission scanning electron microscope, the internal morphological characteristics and internal ring structure characteristics of iron-manganese concretion in the karst area are extracted, and the formation process of iron-manganese concretion in soil of the karst area with high geological background characteristics is deeply researched by combining the color of the concretion under reflected light with the soil formation process in the karst area.

Further, the second axial moving component comprises a sliding bas slidably arranged on the first mounting table, a gear set arranged on the sliding base, a clamping rod set mounted on the gear set, and a first driving motor for supplying power for the gear set.

That is to say, the position of the supporting piece is adjusted through the cooperation of the gear set and the clamping rod set, so that the sample can be subjected to coarse polishing, fine polishing and other steps in turn. Through the arrangement, the grinding efficiency of the sample can be further improved, and high adaptability to later analysis is ensured.

Further, the clamping rod set includes a gear crank with one end capable of being mounted on the gear set, a connecting rod connected with the other end of the gear crank, and a telescopic rod with one end movably arranged on the sliding base and the other end movably arranged on the connecting rod.

That is to say, the position of the telescopic rod is adjusted so that the gear crank moves along the axial direction, and the supporting is further driven to move so that the sample can pass through different grinding pieces in turn to achieve grinding with different grinding degrees. The grinding efficiency of the device is improved by the clamping rod set.

Further, the spring component comprises a plurality of spring pieces circumferentially arranged between the mounting base and the moving base; each of the spring pieces comprises a tripod arranged on the mounting base, and a spring body with one end connected with the tripod and the other end arranged on the moving base.

That is to say, a certain degree of damping can be achieved by the rubber spring, the device can be protected, and the force sensor is prevented from directly acting on the device. At the same time, normal and stable operation of the grinding component is ensured, and then the processing efficiency of the device is improved.

Further, the processing also includes a waste cleaning component. The waste cleaning component includes a blanking port formed in the top of the first mounting table, and a waste collecting tank arranged on the first mounting table and located at the bottom of the blanking port.

That is to say, the waste cleaning component can collect and treat waste generated in the grinding process, so that the waste pollution can be effectively reduced while normal operation of the device is ensured.

Further, the waste collecting tank includes a tank body and a filter screen disc set arranged in the tank body.

That is to say, the waste can be effectively screened through a filter screen to avoid the sample from falling by mistake.

Further, the first axial moving component comprises a bearing table arranged on the first mounting table and a driving rod set arranged on the bearing table.

The number of the driving rod sets is two, and the two driving rod sets are oppositely arranged.

And the number of the closing plates is two, and the two closing plates are arranged on the driving rod sets in one-to-one correspondence.

That is to say, the bearing table is selectively opened according to the grinding thickness, and it is ensured that the grinding thickness of the sample meets the analysis standard, so that the analysis efficiency of the device is improved.

Further, the feeding unit comprises a conveyor belt with one end located at a lower end of the closing plate and the other end extending to the inside of the analyzing component, and a second driving motor for supplying power for the conveyor belt.

That is to say, the automatic design can further improve the analysis efficiency of the device by conveying the sample from the bottom of the bearing table to the analyzing component through the conveyor belt.

Compared with the prior art, the present disclosure has the following beneficial effects. The integral structure of the device is reasonable in design. The collected sample is cleaned and dried in sequence through the pretreatment component and then ground by the processing unit. The force sensor can be adjusted according to a required sample thickness. The sample can be polished step by step by adjusting the position of the sample on the placing piece through the clamping module. The ground sample is sent to the analyzing unit for effective analysis through cooperation of the first feeding unit and the second feeding unit. The sample processing and analyzing device can effectively process a soil concretion sample into a sample for analysis, has the advantages of easy operation, high degree of automation and high efficiency, and is suitable for mass popularization.

Reference signs: 1, mounting unit; 11, first mounting table; 12, second mounting table; 2, processing unit; 20, pretreatment component; 21, first fixed component; 211, first axial component; 2111, bearing table; 2112, driving rod sets; 212, second axial moving component; 2120, sliding base; 2121, gear set; 2122, clamping rod set; 2123, gear crank: 2124, connecting rod; 2125, telescopic rod; 22, second fixed component; 221, radial moving component; 2211, radial mounting guide rail; 2212, moving base; 222, damping component; 2221, mounting base; 2222, spring component; 23, grinding component; 230, feeding device; 2301, electric rotating shaft; 2302, feeding tube; 231, grinding disc; 2311, mounting substrate; 2312, first grinding piece: 2313, second grinding piece; 232, mounting disc; 2320, sample placing groove; 2321, closing plate; 24, waste cleaning component; 241, blanking port; 242, waste collecting tank; 2421, comprises a tank body; 3, analyzing unit; 31, microscope module; 32, photographing module; 4, feeding unit.

DETAILED DESCRIPTION

Embodiment I

Figure 1:
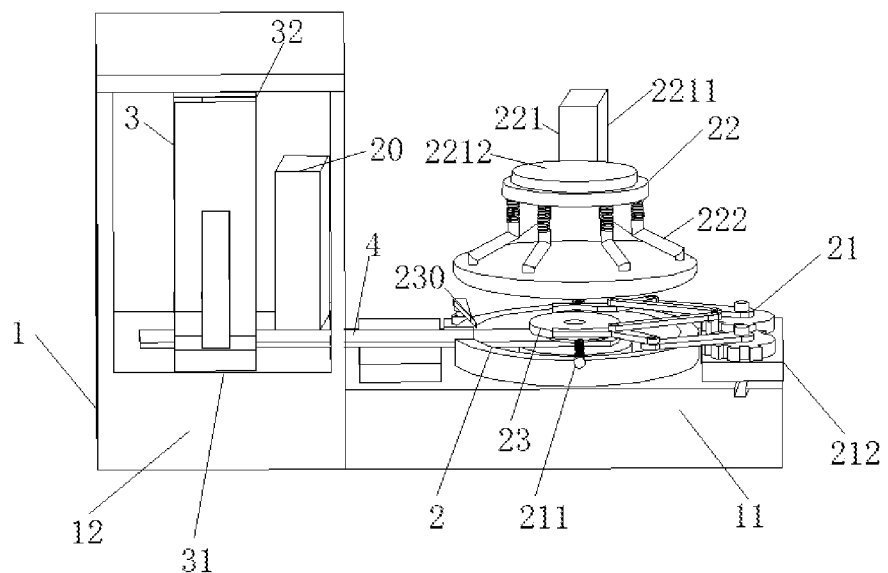
FIG. 1 is a structural schematic diagram of a first embodiment in the present disclosure.

As shown in FIG. 1, a sample processing and analyzing device for soil analysis in a karst area includes a mounting unit 1, a processing unit 2 arranged on the mounting unit 1, and an analyzing unit 3 arranged on the mounting unit 1 and connected with the processing unit 2 through a feeding unit 4.

The mounting unit 1 includes a first mounting table 11 and a second mounting table 12 connected with the first mounting table 11.

The processing unit 2 includes a pretreatment component 20 arranged on the second mounting table 12 and a grinding unit connected with the pretreatment component 20 through the feeding unit 4.

The pretreatment component 20 comprises a treatment cavity arranged on the second mounting table 12, a cleaning module arranged in the treatment cavity and used for cleaning the sample, and an air-drying module arranged on the treatment cavity and used for air-drying the cleaned sample.

The grinding unit comprises a first fixed component 21, a second fixed component 22 and a grinding component 23.

Figure 2:
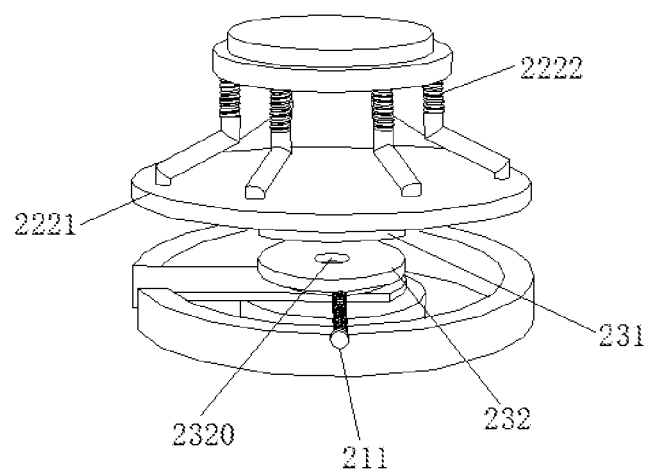
FIG. 2 is a partial schematic diagram of a grinding component in the first embodiment of the present disclosure.

As shown in FIG. 2, the second axial moving component 212 comprises a sliding base 2120 slidably arranged on the first mounting table 11, a gear set 2121 arranged on the sliding base 2120, a clamping rod set 2122 mounted on the gear set, and a first driving motor for supplying power for the gear set.

The clamping rod set 2122 comprises a gear crank 2123 with one end capable of being mounted on the gear set 2121, a connecting rod 2124 connected with the other end of the gear crank 2123, and a telescopic rod 2125 with one end movably arranged on the sliding base 2120 and the other end movably arranged on the connecting rod 2124.

The second fixed component 22 comprises a radial moving component 221 and a damping component 222 arranged on the radial moving component 221: the radial moving component 221 comprises a radial mounting guide rail 2211 and a moving base 2212 arranged on the radial mounting guide rail 2211: the damping component 222 comprises a mounting base 2221 and a spring component 2222 for connecting the mounting base 2221 with the moving base 2212.

The spring component 2222 comprises a plurality of spring pieces circumferentially arranged between the mounting base 2221 and the moving base 2212: each of the spring pieces comprises a tripod arranged on the mounting base 2221, and a spring body with one end connected with the tripod and the other end arranged on the moving base 2212.

Figure 3:
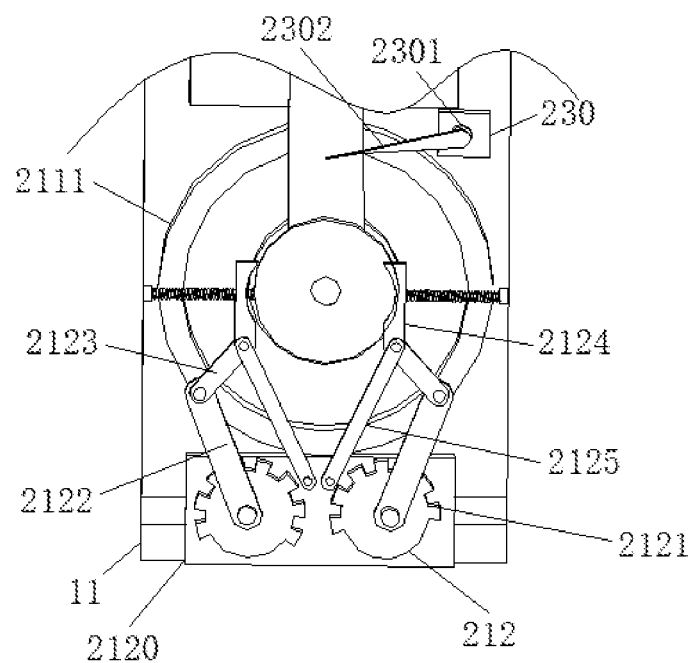
FIG. 3 is a structural schematic diagram of a first fixed component in the first embodiment of the present disclosure.

As shown in FIG. 2, FIG. 3, The grinding component 23 comprises a feeding device 230 arranged on the second mounting table 12, a grinding disc 231 arranged at the bottom of the mounting base 2221, a mounting disc 232 arranged on the second axial moving component 212 and located under the grinding disc 231, and a driving component arranged inside the mounting base 2221 and used for supplying power for the grinding disc 231.

The feeding device 230 comprises a first abrasive storage cavity for storing coarse polishing materials, a second abrasive storage cavity for storing fine polishing materials, and a feeding tube 2302 mounted on the first mounting table 11 through an electric rotating shaft 2301 and used for feeding polishing materials to the sample placed in the sample placing groove 2320: a feeding end of the feeding tube 2302 can be respectively connected with the first abrasive storage cavity and the second abrasive storage cavity.

Among them, the first abrasive storage cavity stores a mixed abrasive of 1-1.5 microns of alumina and silicon carbide in a mass ratio of 1:1, with a grinding disc speed of 400 rpm; The second abrasive storage chamber contains a 1:1 mixture of chromium oxide and iron dichromate, with a grinding disc speed of 600 rpm.

Figure 4:
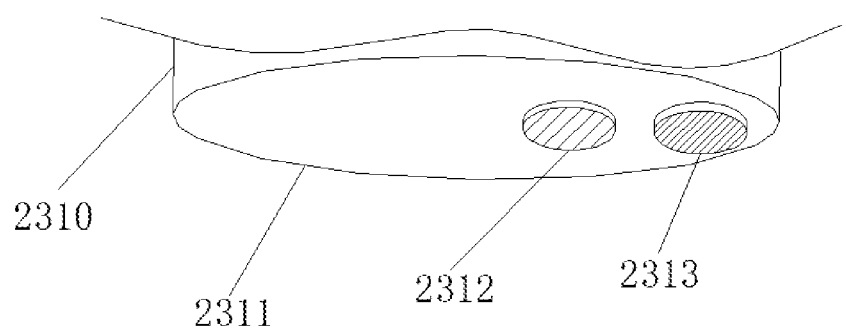
FIG. 4 is a structural schematic diagram of a grinding disc in the first embodiment of the present disclosure.

As shown in FIG. 4, he grinding disc 231 comprises a mounting substrate 2311 arranged at the bottom of the mounting base 2221, and a first grinding piece 2312 and a second grinding piece 2313 axially arranged on the mounting substrate 2311 from inside to outside.

As shown in FIG. 2, a sample placing groove 2320 for placing a sample is formed in the mounting disc 232.

Figure 5:
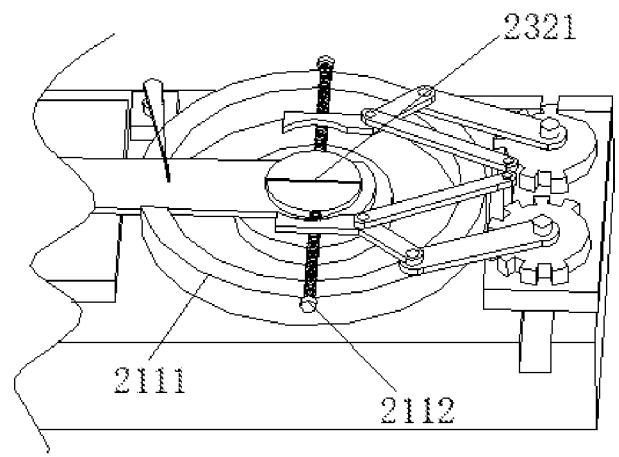
FIG. 5 is a structural schematic diagram of a radial moving component in the first embodiment of the present disclosure.
Figure 6:
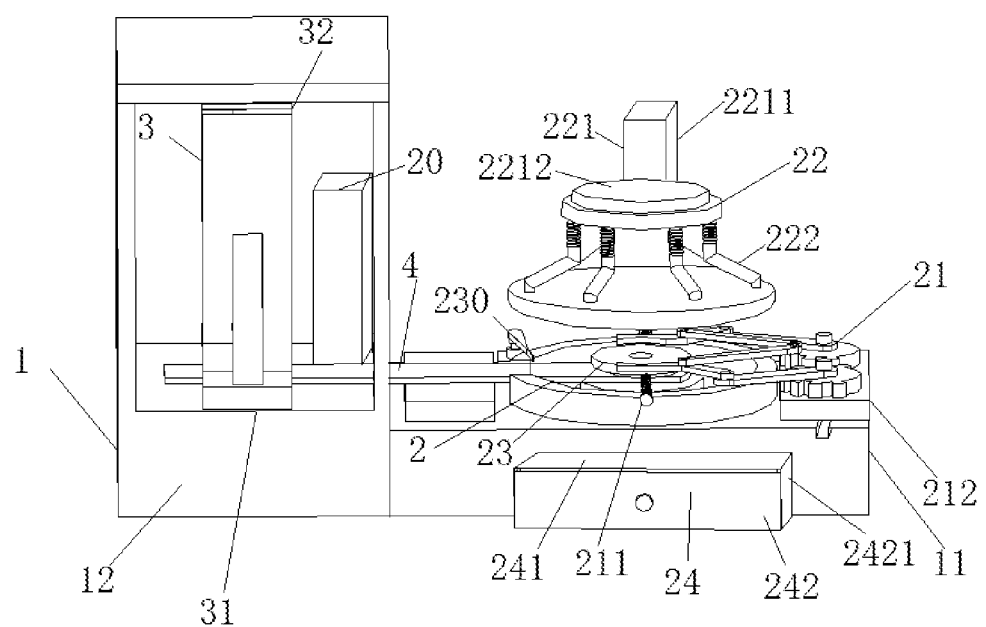
FIG. 6 is a structural schematic diagram of a second embodiment in the present disclosure.

As shown in FIG. 5, The first axial moving component 211 comprises a bearing table 2111 arranged on the first mounting table 11 and a driving rod set 2112 arranged on the bearing table 2111; the number of the driving rod sets 2112 is two, and the two driving rod sets 2112 are oppositely arranged; and the number of the closing plates 2321 is two, and the two closing plates 2321 are arranged on the driving rod sets 2321 in one-to-one correspondence.

As shown in FIG. 1, the analyzing unit 3 includes a microscope module 31 for microscopic observation of the collected sample, and a photographing module 32 for recording observed typical phenomena.

The microscope module 31 includes either one or two of an optical microscope and a field emission scanning electron microscope. The photographing module 32 is a commercially available camera.

The feeding unit 4 comprises a conveyor belt with one end located at a lower end of the closing plate 2321 and the other end extending to the inside of the analyzing component 3, and a second driving motor for supplying power for the conveyor belt.

It should be noted that this embodiment also includes a controller and power supply device. In this embodiment, the first drive motor, second drive motor, drive component, controller, and power supply device are all commercially available products, and the air drying module uses commercially available fans; We won't go into further detail here.

According to the working principle of the embodiment, Place the ferromanganese nodule sample into the processing chamber, clean the sample through a cleaning module, and quickly air dry the sample at room temperature through an air drying module: Then take out the processed sample and place it on the mounting disk 232: Adjust the position of the second fixed component 22 as needed, moving base 2212 vertically along the radial mounting guide rail 2211, drive the grinding disc 231 set at the other end of the damping component 222 to move downwards, and then polish the sample sequentially through the first grinding piece 2312 and the second grinding piece 2313: When performing coarse polishing, rotate the direction of the electric rotating shaft 2301 and use the feeding device 230 to input the polishing material from the first abrasive storage chamber onto the mounting disk 232. Then, adjust the position of the installation disk 232 through the second axial moving component 212 to make the sample rough polished for 2 minutes, and then perform fine polishing. Rotate the direction of the electric rotating shaft 2301 and use the feeding device 230 to input the polishing material from the second abrasive storage chamber onto the mounting disk 232, Clamp the mounting disk 232 through the gear set 2121 and clamping rod set 2122, and then adjust it from the inside out through the sliding base 2120 to fine polish the sample for 2 minutes.

After completing the grinding, adjust the working state of the driving rod group 2112 on the bearing table 2111 to open the closing plate 2321, so that the sample falls from the sample placing groove 2320 in the center of the mounting disk 232 and falls into the conveyor belt.

The samples are transported to the analysis unit 3 at a uniform speed under the action of a conveyor belt, and then analyzed using an optical microscope and a field emission scanning electron microscope on the analysis unit 3. At the same time, the photographing module 32 is used to capture and record the sample status, facilitating further analysis by relevant field workers.

Embodiment II

The difference from the first embodiment lies in that, as shown in FIG. 7, the processing unit 2 also includes a waste cleaning component 24. The waste cleaning component 24 includes a blanking port 241 formed in the first mounting table 11, and a waste collecting tank 242 arranged on the first mounting table 11 and located at the bottom of the blanking port 241. The waste collecting tank 242 includes a tank body 2421 and a filter screen disc set arranged ion the tank body 2421.

The waste cleaning component can collect polished waste, avoid device failures caused by talus accumulation, and further improve the processing efficiency.

The invention claimed is:

1. A sample processing and analyzing device for soil analysis in a karst area, comprising a mounting unit (1), a processing unit (2) arranged on the mounting unit (1), and an analyzing unit (3) arranged on the mounting unit (1) and connected with the processing unit (2) through a feeding unit (4), wherein
the mounting unit (1) comprises a first mounting table (11) and a second mounting table (12) connected with the first mounting table (11);
the processing unit (2) comprises a pretreatment component (20) arranged on the second mounting table (12) and a grinding unit connected with the pretreatment component (20) through the feeding unit (4);
the grinding unit comprises a first fixed component (21), a second fixed component (22) and a grinding component (23);
the first fixed component (21) comprises a first axial component (211) and a second axial moving component (212) respectively arranged on the first mounting table (11);
the second fixed component (22) comprises a radial moving component (221) and a damping component (222) arranged on the radial moving component (221): the radial moving component (221) comprises a radial mounting guide rail (2211) and a moving base (2212) arranged on the radial mounting guide rail (2211): the damping component (222) comprises a mounting base (2221) and a spring component (2222) for connecting the mounting base (2221) with the moving base (2212);
the grinding component (23) comprises a feeding device (230) arranged on the second mounting table (12), a grinding disc (231) arranged at the bottom of the mounting base (2221), a mounting disc (232) arranged on the second axial moving component (212) and located under the grinding disc (231), and a driving component arranged inside the mounting base (2221) and used for supplying power for the grinding disc (231);
the grinding disc (231) comprises a mounting substrate (2311) arranged at the bottom of the mounting base (2221), and a first grinding piece (2312) and a second grinding piece (2313) axially arranged on the mounting substrate (2311) from inside to outside;
a sample placing groove (2320) for placing a sample is formed in the mounting disc (232);
a closing plate (2321) for controlling a port switch at a lower end of the sample placing groove (2320) is arranged on the first axial component (211);
the pretreatment component (20) comprises a treatment cavity arranged on the second mounting table (12), a cleaning module arranged in the treatment cavity and used for cleaning the sample, and an air-drying module arranged on the treatment cavity and used for air-drying the cleaned sample;
the feeding device (230) comprises a first abrasive storage cavity for storing coarse polishing materials, a second abrasive storage cavity for storing fine polishing materials, and a feeding tube (2302) mounted on the first mounting table (11) through an electric rotating shaft (2301) and used for feeding polishing materials to the sample placed in the sample placing groove (2320): a feeding end of the feeding tube (2302) can be respectively connected with the first abrasive storage cavity and the second abrasive storage cavity; and
the analyzing unit (3) comprises a microscope module (31) for microscopic observation of the collected sample, and a photographing module (32) for photographing and recording observed typical phenomena.

2. The sample processing and analyzing device for soil analysis in a karst area according to claim 1, wherein the microscope module (31) comprises either one or two of an optical microscope and a field emission scanning electron microscope.

3. The sample processing and analyzing device for soil analysis in a karst area according to claim 1, wherein the second axial moving component (212) comprises a sliding base (2120) slidably arranged on the first mounting table (11), a gear set (2121) arranged on the sliding base (2120), a clamping rod set (2122) mounted on the gear set, and a first driving motor for supplying power for the gear set.

4. The sample processing and analyzing device for soil analysis in a karst area according to claim 3, wherein the clamping rod set (2122) comprises a gear crank (2123) with one end capable of being mounted on the gear set (2121), a connecting rod (2124) connected with the other end of the gear crank (2123), and a telescopic rod (2125) with one end movably arranged on the sliding base (2120) and the other end movably arranged on the connecting rod (2124).

5. The sample processing and analyzing device for soil analysis in a karst area according to claim 1, wherein the spring component (2222) comprises a plurality of spring pieces circumferentially arranged between the mounting base (2221) and the moving base (2212): each of the spring pieces comprises a tripod arranged on the mounting base (2221), and a spring body with one end connected with the tripod and the other end arranged on the moving base (2212).

6. The sample processing and analyzing device for soil analysis in a karst area according to claim 1, wherein the processing unit (2) also comprises a waste cleaning component (24), the waste cleaning component (24) comprises a blanking port (241) formed in the top of the first mounting table (11), and a waste collecting tank (242) arranged on the first mounting table (11) and located at the bottom of the blanking port (241).

7. The sample processing and analyzing device for soil analysis in a karst area according to claim 6, wherein the waste collecting tank (242) comprises a tank body (2421) and a filter screen disc set arranged in the tank body (2421).

8. The sample processing and analyzing device for soil analysis in a karst area according to claim 1, wherein the first axial moving component (211) comprises a bearing table (2111) arranged on the first mounting table (11) and a driving rod set (2112) arranged on the bearing table (2111);
the number of the driving rod sets (2112) is two, and the two driving rod sets (2112) are oppositely arranged; and
the number of the closing plates (2321) is two, and the two closing plates (2321) are arranged on the driving rod sets (2321) in one-to-one correspondence.

9. The sample processing and analyzing device for soil analysis in a karst area according to claim 1, wherein the feeding unit (4) comprises a conveyor belt with one end located at a lower end of the closing plate (2321) and the other end extending to the inside of the analyzing component (3), and a second driving motor for supplying power for the conveyor belt.

* * * * *